(12) United States Patent
Freeman et al.

(10) Patent No.: US 8,812,236 B1
(45) Date of Patent: Aug. 19, 2014

(54) METHOD FOR USING PARTICLE SIZE ANALYSIS IN NEAR TIME OR REAL TIME TO CREATE A PROPER PARTICLE SIZE DISTRIBUTION WITHIN A DRILLING FLUID MANAGEMENT SYSTEM FOR IMPROVED WELL DRILLING EFFICIENCY

(71) Applicant: Particle Size Engineering, LLC, Houston, TX (US)

(72) Inventors: Thomas W. Freeman, Houston, TX (US); Paula S. DeWitte, Houston, TX (US); Robert W. Troy, Houston, TX (US)

(73) Assignee: Particle Size Engineering, LLC, Houston, TX (US)

( * ) Notice: Subject to any disclaimer, the term of this patent is extended or adjusted under 35 U.S.C. 154(b) by 0 days.

(21) Appl. No.: 14/250,557

(22) Filed: Apr. 11, 2014

(51) Int. Cl.
*E21B 47/00* (2012.01)
*E21B 49/00* (2006.01)
*G01N 15/00* (2006.01)
*B01D 17/12* (2006.01)
*B01D 17/038* (2006.01)
*G01N 15/02* (2006.01)

(52) U.S. Cl.
CPC .................... *E21B 49/00* (2013.01); *G01N 15/02* (2013.01)
USPC ........... 702/6; 73/152.39; 73/152.43; 175/66; 210/739; 210/747.1; 210/787; 210/806; 209/1; 209/155; 702/9; 702/11

(58) Field of Classification Search
CPC .... B01D 17/00; B01D 17/0217; B01D 37/00; B01D 17/12; G01N 15/00; G01N 15/02; G01N 15/0255; G01N 15/0272; G01N 15/06; G01N 15/10; G01N 2015/02; G01N 2015/0277; G01N 2015/0288; E21B 21/06; E21B 21/063; E21B 21/064; E21B 21/065; E21B 47/00; E21B 47/003; E21B 49/005; E21B 49/08; E21B 49/087; E21B 49/088; E21B 47/124; E21B 2049/00; E21B 2049/08; E21B 2049/085
USPC ................. 73/61.71, 152.01, 152.39, 152.42, 73/152.43, 152.55, 152.23, 863.21, 73/863.23; 175/40, 42, 66, 206, 207; 210/739, 740, 747.1, 787, 806; 209/1, 209/155, 546, 551, 724; 702/6, 9, 12, 26, 702/29, 11, 13
See application file for complete search history.

(56) References Cited

U.S. PATENT DOCUMENTS

| | | | | |
|---|---|---|---|---|
| 5,161,409 | A * | 11/1992 | Hughes et al. | 73/152.19 |
| 6,301,953 | B1 * | 10/2001 | Zamfes | 73/38 |
| 7,980,329 | B2 * | 7/2011 | Spiecker et al. | 175/206 |
| 2004/0098202 | A1 * | 5/2004 | McNeil et al. | 702/12 |
| 2006/0200329 | A1 * | 9/2006 | Guo et al. | 703/10 |
| 2011/0220573 | A1 * | 9/2011 | Dixit et al. | 210/639 |
| 2012/0264658 | A1 * | 10/2012 | Kulkarni et al. | 507/138 |
| 2013/0081458 | A1 * | 4/2013 | Mutze et al. | 73/152.02 |
| 2013/0144531 | A1 * | 6/2013 | Johnston | 702/9 |
| 2013/0192360 | A1 * | 8/2013 | Jamison et al. | 73/152.19 |

FOREIGN PATENT DOCUMENTS

GB 2479450 * 10/2011

OTHER PUBLICATIONS

Waldmann et al, "R & D Efforts to Control, Monitor and Identify Drilling Fluid Invasion Into Reservoir Rocks", Paper presented at 1st International Conference on Upstream Engineering and Flow Assurace of the 2012 AIChe Spring Meeting, Houston, Texas, Apr. 1-5, 2012, pp. 1-11.*

Karacan et al, "A fractal model for predicting permeability around perforation tunnels using size distribution of fragmented grains", Journal of Petroleum Science and Enginnering, vol. 40, Jul. 2003, pp. 159-176.*

* cited by examiner

*Primary Examiner* — Joseph Drodge
(74) *Attorney, Agent, or Firm* — Buskop Law Group, PC; Wendy Buskop

(57) ABSTRACT

A method for optimizing drilling fluids by creating a proper particle size analysis and distribution curve of particle sizing within drilling fluid. The particle size distribution curve is maintained with a maximum particle sizing of 6 microns so as to not allow for coarser drilled solids to degrade beyond the point of mechanical separation to prevent a build-up of low gravity solids that can no longer be removed from the drilling fluid during the drilling operation due to their size. An optimal drilling system requires that drilling fluids be modified through the following process to attain the appropriate particle sizing distribution to: make the most efficient use of the drilling operation, reduce the amount to drilling fluids utilized, and reduce formation damage. The method generates corrective actions to modify the drilling fluids or adjust solids control equipment parameters, to obtain a unique particle size distribution throughout the drilling process.

16 Claims, 14 Drawing Sheets

FIGURE 2

| WELL FLUID INFORMATION | 200 |
|---|---|

RIG INFORMATION — 210

| | |
|---:|---|
| RIG NAME: | ☐ 211 |
| WELL NAME: | ☐ 212 |
| DATE/TIME: | ☐ 213 |
| MEASURED DEPTH (FT): | ☐ 28 |
| TRUE VERTICAL DEPTH (FT): | ☐ 26 |
| SAMPLE SOURCE: | ☐ 216 |
| OPERATOR OF THE RIG: | ☐ 217 |

DRILLING FLUID PROPERTIES — 218

MUD DENSITY — 220

| | |
|---:|---|
| MUD WEIGHT IN POUNDS PER GALLON: | ☐ 221 |
| SPECIFIC GRAVITY OF HIGH GRAVITY SOLIDS: | ☐ 222 |
| SPECIFIC GRAVITY OF LOW GRAVITY SOLIDS: | ☐ 223 |
| BASE FLUID WEIGHT IN POUNDS PER GALLON: | ☐ 224 |

RETORT VALUES — 230

| | |
|---:|---|
| OIL CONTENT AS A PERCENT BY VOLUME: | ☐ 231 |
| WATER CONTENT AS A PERCENT BY VOLUME: | ☐ 232 |

CHEMICAL PROPERTIES — 240

| | |
|---:|---|
| CHLORIDE CONTENT IN MILLIGRAMS PER LITER (MG/L): | ☐ 241 |
| ALKALINITY OF THE DRILLING MUD SAMPLE: | ☐ 242 |

SOLIDS ANALYSIS — 250

| | |
|---:|---|
| CORRECTED SOLIDS IN PERCENT BY VOLUME: | ☐ 251 |
| LOW GRAVITY SOLIDS IN PERCENT BY VOLUME: | ☐ 252 |
| HIGH GRAVITY SOLIDS IN PERCENT BY VOLUME: | ☐ 253 |

FIGURE 3

| SOLIDS CONTROL EQUIPMENT INFORMATION | 300 |
|---|---|
| SHAKER 1 INTERFACE | 310 |
| MANUFACTURE NAME: | 311 |
| MODEL NUMBER: | 312 |
| FIRST SHAKER SCREEN: | 313 |
| SECOND SHAKER SCREEN: | 314 |
| THIRD SHAKER SCREEN: | 315 |
| FOURTH SHAKER SCREEN: | 316 |
| TIME STAMP: | 317 |
| DATE STAMP: | 318 |
| SHAKER 2 INTERFACE | 320 |
| MANUFACTURE NAME: | 321 |
| MODEL NUMBER: | 322 |
| FIRST SHAKER SCREEN: | 323 |
| SECOND SHAKER SCREEN: | 324 |
| THIRD SHAKER SCREEN: | 325 |
| FOURTH SHAKER SCREEN: | 326 |
| TIME STAMP: | 327 |
| DATE STAMP: | 328 |
| CENTRIFUGE 1 INTERFACE | 330 |
| MANUFACTURE NAME: | 331 |
| MODEL NUMBER: | 332 |
| GRAVITY FORCE: | 333 |
| CENTRIFUGE 2 INTERFACE | 340 |
| MANUFACTURE NAME: | 341 |
| MODEL NUMBER: | 342 |
| GRAVITY FORCE: | 343 |

FIGURE 8

GRAPHIC TRACK OF PARTICLE SIZE IN MICRONS IN REAL TIME

WARNING

SYMPTOMS:

PROBABLE CAUSES: (PROXIMATE CAUSES)

PROBABLE CAUSES: (ULTIMATE CAUSES)

CORRECTIVE ACTION:

RIG INFORMATION
RIG NAME:
WELL NAME:
DATE/TIME:
MEASURED DEPTH (FT):
TRUE VERTICAL DEPTH (FT):
SAMPLE SOURCE:
OPERATOR OF THE RIG:

REAL TIME PARTICLE SIZE VS. PERCENTILE

| PERCENTILE | SIZE |
|---|---|
| D/10 | |
| D/50 | |
| D/90 | |

MUD DENSITY
MUD WEIGHT IN POUNDS PER GALLON:
SPECIFIC GRAVITY OF HIGH GRAVITY SOLIDS:
SPECIFIC GRAVITY OF LOW GRAVITY SOLIDS:
BASE FLUID WEIGHT IN POUNDS PER GALLON:

RETORT VALUES
OIL CONTENT AS A PERCENT BY VOLUME:
WATER CONTENT AS A PERCENT BY VOLUME:

CHEMICAL PROPERTIES
CHLORIDE CONTENT IN MILLIGRAMS PER LITER (MG/L):
ALKALINITY OF THE DRILLING MUD SAMPLE:

SOLIDS ANALYSIS
CORRECTED SOLIDS IN PERCENT BY VOLUME:
LOW GRAVITY SOLIDS IN PERCENT BY VOLUME:
HIGH GRAVITY SOLIDS IN PERCENT BY VOLUME:

800, 802, 805, 806a, 806b, 808

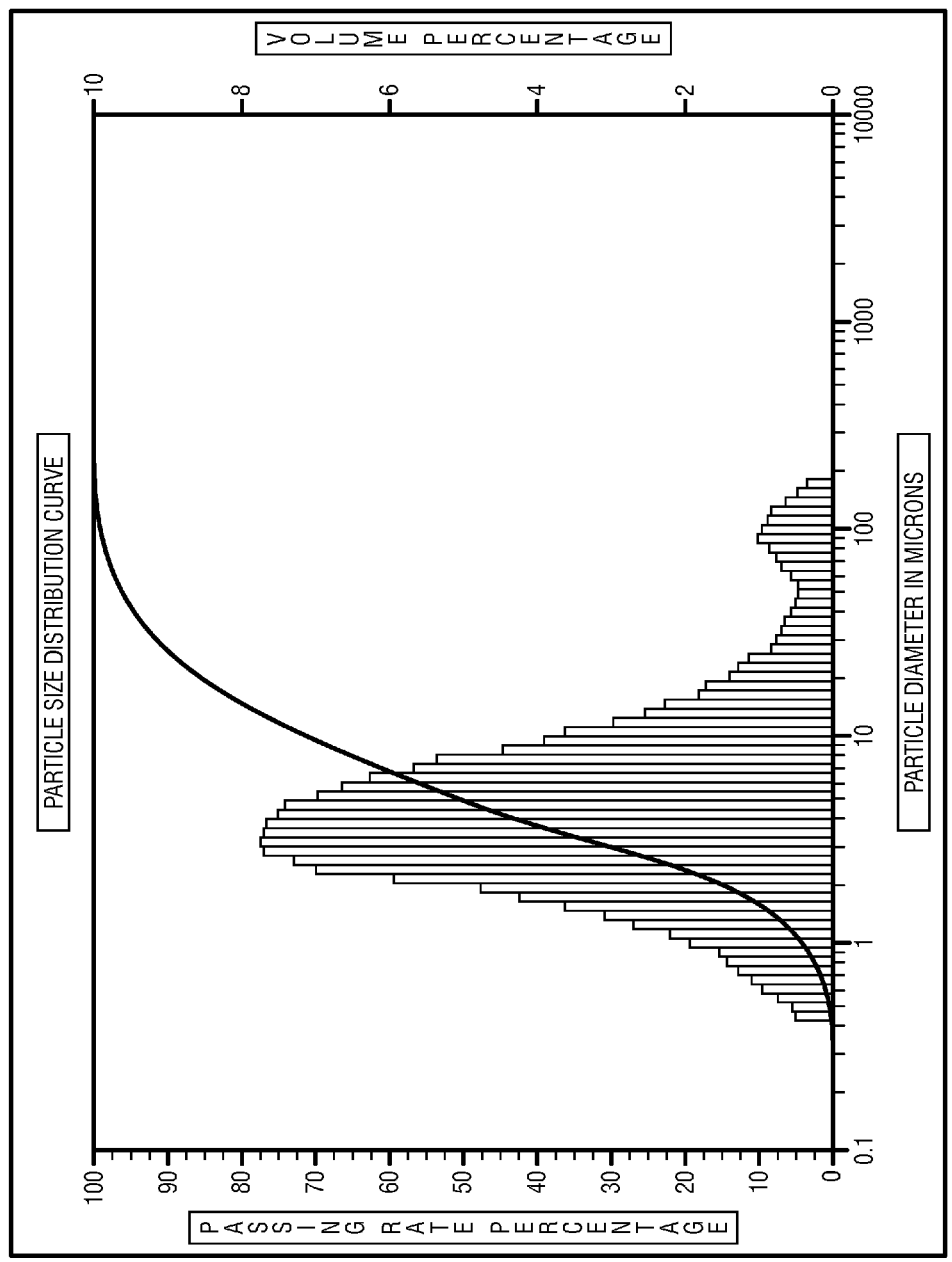

US 8,812,236 B1

METHOD FOR USING PARTICLE SIZE ANALYSIS IN NEAR TIME OR REAL TIME TO CREATE A PROPER PARTICLE SIZE DISTRIBUTION WITHIN A DRILLING FLUID MANAGEMENT SYSTEM FOR IMPROVED WELL DRILLING EFFICIENCY

FIELD

The present embodiments generally relate to a method for using particle size analysis in near time or real time to create a proper particle size distribution curve within a drilling fluid management system for improved well drilling efficiency.

BACKGROUND

A need exists for a reliable method to analyze particle size for drilling mud from a wellbore being drilled after cleaning with a shaker, after cleaning with a centrifuge, and compare analyzed particle size distributions to historic particle size distributions for a wellbore enabling an operator to adjust and optimize the amount and type of cleaning needed and the amount of solids needed for efficiently drilling the wellbore.

The present embodiments meet this need.

BRIEF DESCRIPTION OF THE DRAWINGS

The detailed description will be better understood in conjunction with the accompanying drawings as follows:

FIG. 2 depicts a user interface for inputting well fluid information to the administrative data storage.

FIG. 3 depicts a user interface for inputting solids control equipment information to the administrative data storage.

FIG. 8 depicts a warning message on a display screen.

FIG. 10A depicts a particle size distribution curve associated with Example 1.

Figure 1:
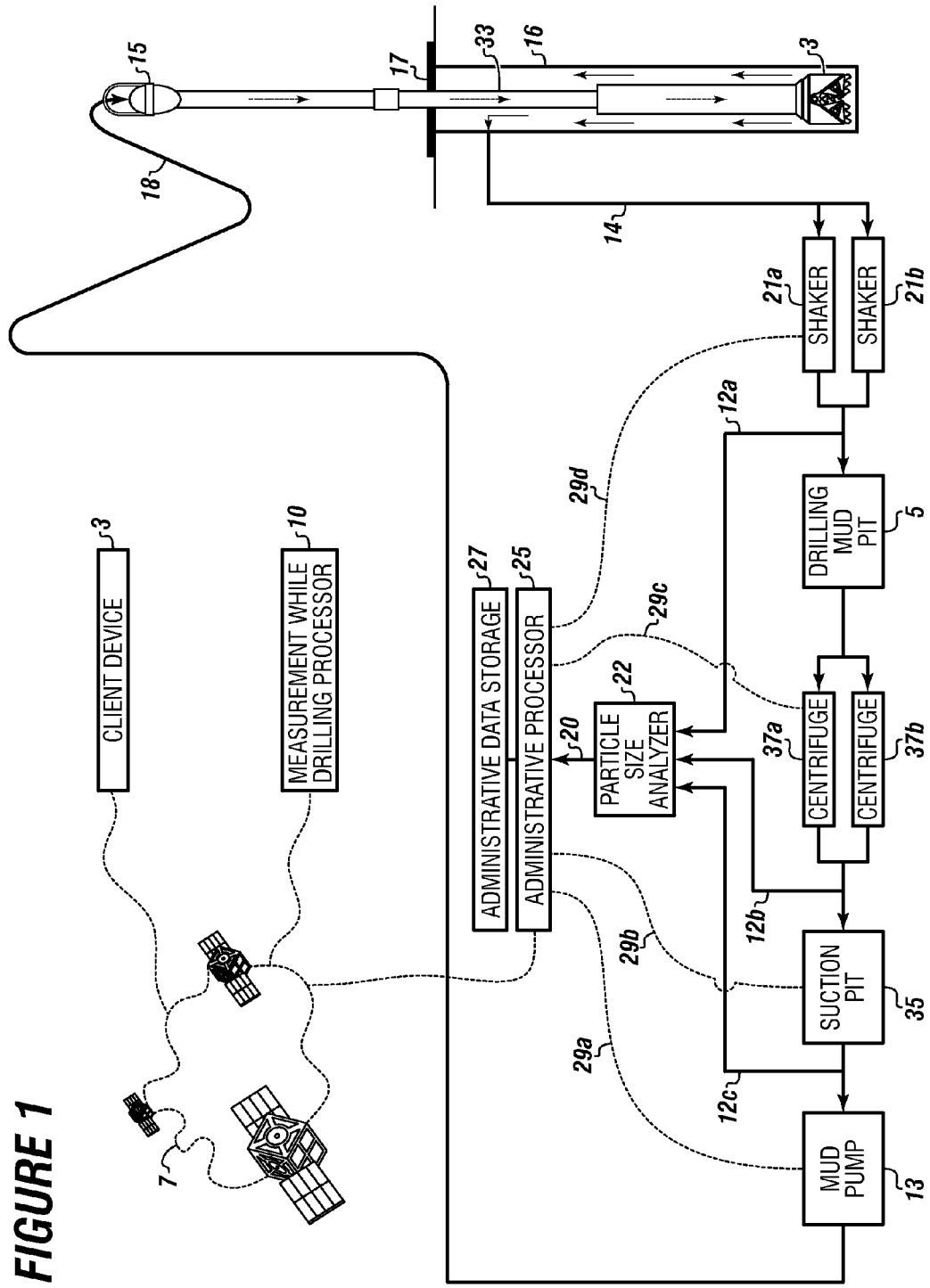
FIG. 1 is a diagram of drilling mud circulation for a wellbore and the equipment usable with the method.

The present embodiments are detailed below with reference to the listed Figures.

DETAILED DESCRIPTION OF THE EMBODIMENTS

Before explaining the present method in detail, it is to be understood that the method is not limited to the particular embodiments and that it can be practiced or carried out in various ways.

Obtaining optimal drilling performance depends on (1) drilling a well as efficiently and at the minimal cost as practical; (2) eliminating time spent correcting drilling issues/problems such as non-productive time (NPT) and invisible lost time (ILT); (3) increasing safety by being able to better control the well and formation pressures to reduce formation damage; and (4) creating the capability to detect early or abnormal well conditions, thus being able to take corrective action and minimizing the probability of an uncontrolled flow from the well.

Drilling fluids are circulated into and out of the wellbore during the drilling process to (1) provide hydrostatic pressure against the formation to prevent formation fluids from entering into the wellbore (i.e., controlling the well and preventing uncontrolled flow from entering the wellbore), (2) lubricate the drill bit thus keeping the drill bit cool and clean during drilling operations, and (3) carry drill cuttings out to the surface to be processed through the surface solids control equipment back to a proper particle size distribution.

The method improves well control during drilling operations. Well control is important because blowouts can kill people. Blowouts have severe environmental impact by polluting water, air, and land.

The method improves safety because fewer drilling days reduces accidents. Well accidents result in explosions which can cause death or injury to rig workers. Accidents also have severe environmental impact by polluting water, air, and land.

The method reduces the number of days required to drill wells. Reducing the numbers of days reduces costs. This results in cheaper oil and gas products to the consumer.

The method decreases the amount of contaminated drilling fluids produced. Contaminated drilling fluids must be treated and disposed of. The treatment and disposal pollutes the water and land.

The method has high economic benefits to the operator to allow the recovery of additional reserves for production through allowing more wells to be drilled with the same dollars.

The method enables ultra-extended reach drilling, reliable and efficient drilling operations in difficult environments including offshore and deep water applications, and generates cost reduction, safety, and operational improvements throughout the drilling operations.

Drilling fluids are often referred to in the drilling industry as "mud."

Drilling fluids are composed of water, solids, additive chemicals, other additives, and occasionally very small percentage of oil.

Drilling fluids can contain weighting agents (i.e., particles) to create the hydrostatic head (pressure required to counterbalance the formation pressure) to prevent the formations from creating and uncontrolled flow into the wellbore and a loss of well control.

Weighting agents are additives to drilling fluids that are typically suspended in the drilling fluid used to increase the density and ultimately increase the hydrostatic pressure needed to balance equally formation pressures (i.e., balance drilling).

Solids control equipment is used at the drilling rig to separate the drilling cuttings from the drilling fluids that are generated at the drill bit and carried to the surface for separation.

Solid control equipment can include a mud tank, shale shaker, vacuum degasser, desander, desilter, hydro cyclones, centrifuges, and other equipment.

When utilized together, the entire solids control equipment package has the ability to create the proper particle size distribution for the drilling fluid within a well.

Chemicals (e.g., salt, clay, barite, lime, and emulsifier) can be added to the drilling fluids after passing through the solids control equipment and before the drilling fluids are returned to the wellbore to obtain the proper weighting of the drilling mud and obtaining the proper particle size distribution curve for increased drilling efficiency.

The method addresses a newly discovered area of improving drilling efficiency by optimizing current drilling fluids best practices to create suitable particle size distributions (PSD) for the drilling fluid throughout the drilling process.

Particle size analysis (PSA) is the process to determine the size range and average or mean size of particles in a drilling fluid sample.

While the maximum particle size for the particle size distribution curve should not be greater than 6 microns, however, a maximum particle size for the particle size distribution of less than approximately 12 microns will still greatly increase the efficiency of the well drilling and reduce costs.

Adding the use of the particle size distribution curves for the drilling fluids to current best practices for drilling a well results in a 20 percent improvement in drilling Current industry emphasis on drilling efficiency is not on optimizing the particle size distribution curve, but rather on (1) removing drilling cuttings or (2) adding or removing ingredients from the drilling fluids.

Current drilling industry practice does not utilize particle size analysis for drilling fluid management. Conventional drilling practices typically focus on increasing drilling rates to attempt to increase drilling efficiency.

Standard drilling fluid practices are based upon analyzing the drilling fluids a few to several times a day and do not include particle size analysis.

Current best practices modify the chemical composition of drilling fluids (1) by adding or removing other chemicals during the drilling process; (2) by removing drilling cuttings; or (3) by adding base fluid.

When a drilling fluid sample is sent to an offsite laboratory for an analysis, a particle size distribution curve can be created, but is usually several days out of date from what is actually happening at the well site.

In addition to non-productive time and invisible lost time, poor drilling fluid properties, practices, and fluid maintenance result in (1) poor drilling efficiency, (2) excessive use of base fluid chemicals, (3) drill bit wear, (4) excess/unnecessary contaminated waste to be disposed, (5) drilling performance problems such as stuck pipe, and (6) circulation issues such as uncontrolled flow into or from the formation.

The method creates a 20 percent increase in capital efficiency which contributes directly to the profitability of the oil and gas drilling company.

The method will enable oil and gas producers to drill more wells for the same cost, that is, for the cost of drilling 100 wells, 120 can now be drilled for the same cost.

Use of the method will enable oil and gas producers to improve company net revenue, improve the return on investment, and ultimately improve the share price if the company is a publically traded company.

Use of this method will increase the value of an owner's equity position in their oil and gas producing company.

Embodiments of the method will significantly reduce the amount of unnecessary contaminated drilling fluids and the associated transportation and disposal costs.

Embodiments of the method will reduce the number of days required to drill in extreme or fragile environments (i.e., deep-water, the arctic, or by fracking) resulting in reducing the risk to safety and/or environmental hazards and accidents.

The method is based on using currently available particle size measurement equipment to measure the particle size distribution within the drilling fluid to derive a proper particle size distribution curve.

When utilizing conventional industry practice, the finer particulates (particles) increase the plastic viscosity defined as the force required to initiate fluid flow relative to the amount, size, and shape of the particles in suspension in the drilling mud.

Generally, as the particle sizes become finer due to mechanical/chemical degradation, the particle size distribution will show an increase of finer solids and reduction of coarser solids.

The plastic viscosity can increase; however, finer distributions of more inert solids less than 6 microns (such as: weighting agents such as barite, hematite) will not cause dramatic increases in plastic viscosity as reactive solids will. This allows for higher concentrations of inert solids without the same negative effects on plastic viscosity as seen using reactive solids.

From the analysis of the particle size distribution curve of the drilling fluids and drilling fluid properties, corrective actions to the drilling fluid's particle size distribution can be identified and corrected through the use of solids control equipment.

Based on the analysis of the drilling fluids composition and particle size distribution, the drilling fluid is decontaminated (removal of drilling cuttings and unwanted particle sizes) throughout the drilling process by processing the drilling fluid through the solid control equipment to separate and remove particles to meet the desired particle size distribution for optimal drilling efficiency prior to the drilling fluid being allowed to return to the wellbore. Drilling efficiency can refer to various monitored parameters which can include, but are not limited to, the following: drill bit penetration, well control, and reduction of non-productive time or invisible lost time during drilling operations.

Fluid properties during the particle sizing optimization are to be maintained in accordance with standard industry practices to include but not limited to density, viscosity, plastic viscosity, yield point, salinity, alkalinity, electric stability, hardness, gel strength, oil/water ratio, corrected solids, total solids, and cake thickness.

The method, in conjunction with using the current inputs from the drilling rig (e.g., mud weight and current drilling penetration rate), will determine the best possible corrective actions, such as modifying the drilling fluids, adjusting solids control equipment parameters, or modifying the drilling program/parameters.

This method in part uses a knowledge based system that when utilized properly with solids control equipment will create a continuous improvement loop to continually optimize the drilling fluid's particle size distribution. The knowledge system includes a set of rules in the data storage of the administrative processor used by the method.

The invention, when utilized along with best industry practices for the drilling fluid, will formulate and present to a user the corrective actions necessary utilizing the solids control equipment to create the optimal particle size distribution for the drilling fluid.

Although drilling fluids are most often associated with oil and gas applications, drilling fluids are used in any application of drilling through the Earth's formation for a well to include but not limited to drilling water wells, hydrothermal wells, or wells to deposit high level nuclear waste.

The following definitions are used herein:

The term "alkalinity" as used herein refers to a chemical property of an aqueous system that implies that there are more hydroxyl ions (OH−) in the system, or a potential to produce more hydroxyl ions, than there are hydrogen ions (H+), or potential to produce hydrogen ions.

The term "barite" as used herein refers to a dense mineral comprising barium sulfate [BaSO4]. Commonly used as a weighting agent for all types of drilling fluids, barites are mined in many areas worldwide and shipped as ore to grinding plants in strategic locations. Contaminants in barite, such as cement, siderite, pyrrhotite, gypsum, and anhydrite, can cause problems in certain mud systems and should be evaluated in any quality assurance program for drilling-mud additives.

The term "borehole or wellbore" as used herein refers to an open hole or uncased portion of the well. Borehole can refer to the inside diameter of the wellbore wall, the rock face that bounds the drilled hole.

The term "cake thickness" refers to the measurement of the thickness of the filter cake, usually recorded in 1/32 of an inch. Under dynamic conditions, filter-cake thickness depends on rate of deposition versus erosion caused by fluid circulation and mechanical abrasion by the rotating drillstring. Typically, the filter cake will reach an equilibrium thickness in the wellbore. In laboratory tests, however, filter cake is built under static conditions with no erosion.

The term "centrifuge" as used herein refers to an item of solids-removal equipment that removes fine and ultrafine solids. It consists of a conical drum that rotates at 2000 rpm to 4000 rpm. Drilling fluid is fed into one end and the separated solids are moved up the bowl by a rotating scroll to exit at the other end. Centrifuges generally have limited processing capacity (50 gpm to 250 gpm) but are useful for processing weighted drilling fluids and can remove finer solids than can a hydrocyclone or shaker screens. They can also be used for water clarification or for processing oily cuttings.

The term "centrifuge interface" refers to information input into a database in the administrative data storage that includes manufacturer name, model number, gravity force, time stamp, and date stamp.

The term "client device" refers to a computer, a laptop, a tablet, a smartphone, or other device with a processor or ability for bi-directional data communication.

The term "cut point" refers to the minimum point of mechanical separation for a given particulate removal device.

The term "density" refers to a unit of mass per unit of volume. Density is typically reported in g/cm3 (for example, rocks) or pounds per barrel (drilling mud) in the oil field.

The term "drill bit" as used herein refers to a tool used to crush or cut rock. Everything on a drilling rig directly or indirectly assists the bit in crushing or cutting the rock. The bit is on the bottom of the drill string and must be changed when it becomes excessively dull or stops making progress. Most bits work by scraping or crushing the rock, or both, usually as part of a rotational motion. Some bits, known as hammer bits, pound the rock vertically in much the same fashion as a construction site air hammer.

The term "drill pipe" refers to a tubular steel conduit fitted with special threaded ends called tool joints. The drill pipe connects the rig surface equipment with the bottom hole assembly and the bit, both to pump drilling fluid to the bit and to be able to raise, lower and rotate the bottom hole assembly and bit.

The term "drilling fluid" refers to any of a number of liquid and gaseous fluids and mixtures of fluids and solids (as solid suspensions, mixtures and emulsions of liquids, gases and solids) used in operations to drill boreholes into the earth. Synonymous with "drilling mud" in general usage, although some prefer to reserve the term "drilling fluid" for more sophisticated and well-defined "muds." Classifications of drilling fluids have been attempted in many ways, often producing more confusion than insight. One classification scheme, given here, is based only on the mud composition by singling out the component that clearly defines the function and performance of the fluid: (1) water-base, (2) non-water-base, and (3) gaseous (pneumatic). Each category has a variety of subcategories that overlap each other.

The term "drilling rig" refers to the machine used to drill a wellbore. In onshore operations, the rig includes virtually everything except living quarters. Major components of the rig include the mud tanks, the mud pumps, the derrick or mast, the drawworks, the rotary table or top drive, the drill string, the power generation equipment and auxiliary equipment. Offshore, the rig includes the same components as onshore, but not those of the vessel or drilling platform itself. The rig is sometimes referred to as the drilling package, particularly offshore.

The term "emulsifier" refers to a chemical additive that creates an emulsion, a dispersion of one immiscible liquid into another, by reducing the interfacial tension between the two liquids to achieve stability. Two emulsion types are used as muds: (1) oil-in-water (or direct) emulsion, known as an "emulsion mud" and (2) water-in-oil (or invert) emulsion, known as an "invert emulsion mud." The former is classified as a water-base mud and the latter as an oil-base mud.

The term "fine solids" or "fines" refers to the size of solids below the cut point of screens.

The term "ultrafines" refers to the size of solids below the cut point of solids equipment control which utilizes centrifugal force.

The term "fluid loss" refers to a leakage of the liquid phase of drilling fluid, slurry or treatment fluid containing solid particles into the formation matrix. The resulting buildup of solid material or filter cake may be undesirable, as may the penetration of filtrate through the formation. Fluid-loss additives are used to control the process and avoid potential reservoir damage.

The term "gravity force or gravity" refers to the force exerted measured by the Earth's gravitational field, or the attractive force produced by the mass of the Earth. Variations in the gravitational field can be used to map changes in the density of formations in the Earth. Solids control equipment uses gravity force to separate particles suspended in fluid.

The term "hematite" as used herein refers to the mineral form of ferric oxide [Fe2O3]. The hematite ore used as a weighting material in drilling muds has a mica-like crystal structure that grinds to particle size suitable for use in drilling fluids. To check for potential wear, an abrasion test is usually run on hematite as a quality control pilot test.

The term "high gravity solids" refers to dense solids, such as barite or hematite, which are added to a mud to increase its density, also known as weighting material. The concentration of high-gravity solids in a weighted mud is measured by the mud engineer daily using mud weight, retort data, chloride titration data and other information. Solids are reported as lb/bbl or volume percent. The specific gravity of water is 1.00, barite is 4.20, and hematite 5.505 g/cm3. Drill solids and other low-gravity solids are normally assumed to be 2.60 g/cm3

The term "lithology" refers to the composition or type of rock and their characteristics.

The term "low gravity solids" refers to a type of drilling-fluid solid having a lower density than barite or hematite, including drill solids and mud additives not including weighting agents. The mud engineer calculates the concentration of these and other types of solids on the basis of mud weight, retort analysis, chloride titrations and other information. Solids are reported as lb/bbl or volume percent. Water is 1.0, barite 4.20, and hematite 5.505 g/cm3. Low-gravity solids are normally assumed to have a density of 2.60 g/cm3.

The term "low specific gravity solids" refers a type of drilling-fluid solid having a lower density than the barite or hematite that is used to weight up a drilling fluid, including drill solids plus the added bentonite clay. The mud engineer calculates the concentration of these and other types of solids on the basis of mud weight, retort analysis, chloride titrations and other information. Solids are reported as lb/bbl or volume percent. Water is 1.0, barite 4.20, and hematite 5.505 g/cm3. Low-gravity solids are normally assumed to have a density of 2.60 g/cm3.

The term "measured depth" refers to the length of the wellbore, as if determined by a measuring stick. This measurement differs from the true vertical depth of the well in all but vertical wells. Since the wellbore cannot be physically measured from end to end, the lengths of individual joints of drill pipe, drill collars and other drill string elements are measured with a steel tape measure and added together. Importantly, the pipe is measured while in the derrick or laying on a pipe rack, in an untensioned, unstressed state. When the pipe is screwed together and put into the wellbore, it stretches under its own weight and that of the bottom hole assembly. Although this fact is well established, it is not taken into account when reporting the well depth. Hence, in virtually all cases, the actual wellbore is slightly deeper than the reported depth.

The term "mechanical separation" refers to physically separating solids suspended in a fluid using centrifugal force or screens.

The term "mud" refers to a drilling fluid that is transferred downhole, especially fluids that contain significant amounts of suspended solids, emulsified water or oil. Mud includes all types of water-base, oil-base and synthetic-base drilling fluids. Drill-in, completion and workover fluids are sometimes called muds, although a fluid that is essentially free of solids is not strictly considered mud.

The term "mud additive" refers to a material added to a drilling fluid to perform one or more specific functions, such as a weighting agent, viscosifier or lubricant The term "mud pump" refers to a mud pump is a large reciprocating pump used to circulate the mud (drilling fluid) on a drilling rig. It is an important part of the oil well drilling equipment The term "mud report" refers to the report sheets filled out by the mud engineer at the well site on a daily basis. The mud report supplies results of tests performed several times per day as well as details about mud product usage, inventory, recommendations and other pertinent information. Multiple-copy forms in a format approved by the American Petroleum Institute (API), which are provided by the mud service company, are the traditional type of mud report. Today, mud reports are more likely to be computerized and transmitted electronically.

The term "mud weight" refers to the mass per unit volume of a drilling fluid, synonymous with mud density. Weight is reported in lb/gal (also known as ppg), kg/m3 or g/cm3 (also called specific gravity or SG), lb/ft3 or in hydrostatic gradient, lb/in2/ft (psi/ft) or pptf (psi/1000 ft). Mud weight controls hydrostatic pressure in a wellbore and prevents unwanted flow into the well. The weight of the mud also prevents collapse of casing and the open hole. Excessive mud weight can cause lost circulation by propagating, and then filling, fractures in the rock. Mud weight (density) test procedures using a mud balance have been standardized and published by the American Petroleum Institute.

The term "network" refers to a global communication network, such as the internet, a local area network, an intranet, a wide area network, a satellite network, a Bluetooth network, a Wi-Fi network, a similar network or combinations thereof.

The term "particle size analyzer" refers to a specialized piece of equipment to conduct analysis on samples or sample streams to determine the size and distribution of particles within that sample.

The term "particle size distribution" refers to the weight, or net volume, of solid particles that fall into each of the various size ranges, given as a percentage of the total solids of all sizes in the sample of interest. Particle size can be determined by sieve analysis, light scattering, passage through an electrically charged orifice, settling rate or other methods. Data are typically shown as a histogram chart with percentage-smaller-than on the y-axis and size ranges on the x-axis. Mud engineers use such data to operate solids-control equipment effectively. Particle size distributions are used to evaluate bridging materials for drill-in and completion fluids. Barite and hematite samples are examined to ensure performance without excessive wear on equipment and as an American Petroleum Institute/International Standards Organization (API/ISO) quality specification.

The term "particulate removal device" refers to at least one shaker receiving used drilling mud from the wellbore, and at least one centrifuge fluidly connected to a drilling mud pit that receives drilling mud with at least some particulates removed by at least one shaker.

The term "penetration rate" refers to the speed at which the drill bit can break the rock under it and thus deepen the wellbore. This speed is usually reported in units of feet per hour or meters per hour.

The term "rate of penetration" refers to the speed at which the drill bit can break the rock under it and thus deepen the wellbore. This speed is usually reported in units of feet per hour or meters per hour.

The term "reactive solids" refers to commercial additives, drilled solids, and clays that react vigorously to moisture and other substances.

The term "real time data" refers to measurements-while-drilling (MWD) and logging while drilling, the data transmitted to surface shortly after being recorded. These are distinct from the data recorded into memory. Only a subset of the recorded data can be transmitted as real-time data because of the limited data rate of measurements-while-drilling telemetry systems. This reduces the number of channels, the sample interval, or both, in the real-time data.

The term "retention time" refers to an amount of time a liquid stays in a vessel. The retention time assures that equilibrium between the liquid and gas has been reached at separator pressure. The retention time in a separator is determined by dividing the liquid volume inside the vessel by the liquid flow rate. The retention time usually varies from 30 seconds to 3 minutes. If a foaming crude is present, the retention time can be increased by four times its normal values.

The term "rheology" refers to deformation and flow of matter. Rheology is an extremely important property of drilling muds, drill-in fluids, workover and completion fluids, cements and specialty fluids and pills. Mud rheology is measured on a continual basis while drilling and adjusted with additives or dilution to meet the needs of the operation. In water-base fluids, water quality plays an important role in how additives perform. Temperature affects behavior and interactions of the water, clay, polymers and solids in a mud. Downhole pressure must be taken into account in evaluating the rheology of oil muds.

The term "rotary table" refers to the revolving or spinning section of the drill floor that provides power to turn the drill string in a clockwise direction (as viewed from above). The rotary motion and power are transmitted through the kelly bushing and the kelly to the drill string. When the drill string is rotating, the drilling crew commonly describes the operation as simply, "rotating to the right," "turning to the right," or, "rotating on bottom." Almost all rigs today have a rotary table, either as primary or backup system for rotating the drill string. Top drive technology, which allows continuous rotation of the drill string, has replaced the rotary table in certain operations. A few rigs are being built today with top drive systems only, and lack the traditional kelly system.

The term "salinity" refers to a saltiness or dissolved salt content.

The term "salt" refers to the product formed by neutralization of an acid and a base. The term is more specifically applied to sodium chloride. Neutralization is an important reaction in many aspects of mud control and treatment.

The term "sample source" refers to a drilling mud sample as collected from a shaker, a centrifuge after being treated by a shaker, or a drilling mud sample as collected from a suction pit after being treated sequentially by a shaker and a centrifuge.

The term "shaker" refers to shale shaker, the primary and probably most important device on the rig for removing drilled solids from the mud. This vibrating sieve is simple in concept, but a bit more complicated to use efficiently. A wire-cloth screen vibrates while the drilling fluid flows on top of it. The liquid phase of the mud and solids smaller than the wire mesh pass through the screen, while larger solids are retained on the screen and eventually fall off the back of the device and are discarded. Obviously, smaller openings in the screen clean more solids from the whole mud, but there is a corresponding decrease in flow rate per unit area of wire cloth. Hence, the drilling crew should seek to run the screens (as the wire cloth is called), as fine as possible, without dumping whole mud off the back of the shaker. Where it was once common for drilling rigs to have only one or two shale shakers, modern high-efficiency rigs are often fitted with four or more shakers, thus giving more area of wire cloth to use, and giving the crew the flexibility to run increasingly fine screens.

The term "shaker interface" refers to information input into a database in the administrative data storage that includes manufacturer name, model number, first shaker screen, second shaker screen, third shaker screen, fourth shaker screen, time stamp, and date stamp.

The term "shale shaker" refers to a vibrating sieve is simple in concept, but a bit more complicated to use efficiently. A wire-cloth screen vibrates while the drilling fluid flows on top of it. The liquid phase of the mud and solids smaller than the wire mesh pass through the screen, while larger solids are retained on the screen and eventually fall off the back of the device and are discarded. Smaller openings in the screen clean more solids from the whole mud, but there is a corresponding decrease in flow rate per unit area of wire cloth. Therefore, the drilling crew should seek to run the screens (as the wire cloth is called), as fine as possible, without dumping whole mud off the back of the shaker. Where it was once common for drilling rigs to have only one or two shale shakers, modern high-efficiency rigs are often fitted with four or more shakers, thus giving more area of wire cloth to use, and giving the crew the flexibility to run increasingly fine screens.

The term "shear rate" refers to the velocity gradient measured across the diameter of a fluid-flow channel, be it a pipe, annulus or other shape. Shear rate is the rate of change of velocity at which one layer of fluid passes over an adjacent layer. As an example, consider that a fluid is placed between two parallel plates that are 1.0 cm apart, the upper plate moving at a velocity of 1.0 cm/sec and the lower plate fixed. The fluid layer at the lower plate is not moving and the layer nearest the top plate is moving at 1.0 cm/sec. Halfway between the plate, a layer is moving at 0.5 cm/sec. The velocity gradient is the rate of change of velocity with distance from the plates. This simple case shows the uniform velocity gradient with shear rate (v1−v2)/h=shear rate=(cm/sec)/(cm/1)=1/sec. Hence, shear rate units are reciprocal seconds.

The term "shear stress" refers to the force per unit area required to sustain a constant rate of fluid movement. Mathematically, shear stress can be defined as: if a fluid is placed between two parallel plates space 1 cm apart and a force of 1 dyne is applied to each square centimeter of the upper plate to keep it in motion, the shear stress in the fluid is 1 dyne/cm squared at any point between the two plates.

The term "solids control equipment" reefers to equipment used within a solid control system which includes: the mud tank, shale shaker, vacuum degasser, desander, desilter, and centrifuge.

The term "standpipe" refers to a rigid metal conduit that provides the high-pressure pathway for drilling mud to travel approximately one-third of the way up the derrick, where it connects to a flexible high-pressure hose (kelly hose). Many large rigs are fitted with dual standpipes so that downtime is kept to a minimum if one standpipe requires repair.

The term "true vertical depth" refers to the vertical distance from a point in the well (usually the current or final depth) to a point at the surface, usually the elevation of the rotary kelly bushing (RKB). This is one of two primary depth measurements used by the drillers, the other being measured depth. True vertical depth is important in determining bottom hole pressures, which are caused in part by the hydrostatic head of fluid in the wellbore. For this calculation, measured depth is irrelevant and true vertical depth must be used. For most other operations, the driller is interested in the length of the hole or how much pipe will fit into the hole. For those measurements, measured depth, not true vertical depth, is used. While the drilling crew should be careful to designate which measurement they are referring to, if no designation is used, they are usually referring to measured depth. Note that measured depth, due to intentional or unintentional curves in the wellbore, is always longer than true vertical depth.

The term "viscosifiers" refers to material in the drilling mud that alters its viscosity. Viscosity is defined as a property of fluids and slurries that indicates their resistance to flow, defined as the ratio of shear stress to shear rate. Viscosity can be expressed mathematically as follows: poise is the unit for viscosity, equivalent to dyne-sec/cm2. Because one poise represents a high viscosity, 1/100 poise, or one centipoise (cp), is used for mud measurements. One centipoise equals one millipascal-second. Viscosity must have a stated or an understood shear rate in order to be meaningful. Measurement temperature also must be stated or understood.

The term "viscosity" refers to a property of fluids and slurries that indicates their resistance to flow, defined as the ratio of shear stress to shear rate. Viscosity can be expressed mathematically as follows: poise is the unit for viscosity, equivalent to dyne-sec/cm2. Because one poise represents a high viscosity, 1/100 poise, or one centipoise (cp), is used for mud measurements. One centipoise equals one millipascal-second. Viscosity must have a stated or an understood shear rate in order to be meaningful. Measurement temperature also must be stated or understood.

The term "weighting agents" refers to weighting material, a high-specific gravity and finely divided solid material used to increase density of a drilling fluid. (Dissolved salts that increase fluid density, such as calcium bromide in brines, are not called weighting materials.) Barite is the most common, with minimum specific gravity of 4.20 g/cm3. Hematite is a more dense material, with minimum specific gravity of 5.05 g/cm3, per American Petroleum Institute (API) and International Standards Organization (ISO) specifications. Calcium carbonate, specific gravity 2.7 to 2.8, is considered weighting material but is used more for its acid solubility than for density. Siderite, specific gravity around 3.8, has been used to densify mud, but can cause problems by dissolving into the mud at high pH. Ilmenite, specific gravity of 4.6 has been used in drilling fluid and cement. Only barite and hematite have American Petroleum Institute/International Standards Organization (API/ISO) standards.

The term "weighting materials" refer to high-specific gravity and finely divided solid material used to increase density of a drilling fluid. (Dissolved salts that increase fluid density, such as calcium bromide in brines, are not called weighting materials.) Barite is the most common, with minimum specific gravity of 4.20 g/cm3. Hematite is a more dense material, with minimum specific gravity of 5.05 g/cm3, per American Petroleum Institute (API) and ISO specifications. Calcium carbonate, specific gravity 2.7 to 2.8, is considered weighting material but is used more for its acid solubility than for density. Siderite, specific gravity around 3.8, has been used to densify mud, but can cause problems by dissolving into the mud at high pH. Ilmenite, specific gravity of 4.6 has been used in drilling fluid and cement. Only barite and hematite have American Petroleum Institute/International Standards Organization (API/ISO) standards The term "well control" refers to focused on maintaining pressure on open formations (exposed to the wellbore) to prevent or direct the flow of formation fluids into the wellbore. This technology encompasses the estimation of formation fluid pressures, the strength of the subsurface formations and the use of casing and mud density to offset those pressures in a predictable fashion. Also included are operational procedures to safely stop a well from flowing should an influx of formation fluid occur. To conduct well-control procedures, large valves are installed at the top of the well to enable well site personnel to close the well if necessary.

The term "wellbore" refers to the drilled hole or borehole, including the open hole or uncased portion of the well. Borehole can refer to the inside diameter of the wellbore wall, the rock face that bounds the drilled hole.

The term "yield point" refers to the ability of drilling fluids to carry drilled cuttings to the surface.

Turning now to the Figures, FIG. 1 is a diagram of drilling mud circulation for a wellbore and the equipment usable with the method.

Cleaned drilling mud 18 is piped from a suction pit 35 by a mud pump 13 to a swivel 15 connected to a kelly bushing 17 for then entering drill pipe 33 that is run into a wellbore 16. The cleaned drilling mud 18 flows down the wellbore to a drill bit 3.

Used drilling mud 14 is pulled back out of the wellbore and a plurality of drilling mud samples 12a-12c are then analyzed by the method to produce data 20 that presents drilling mud particle size after different stages of cleaning, by shaker and by centrifuge. After shaking and cleaning, the cleaned drilling mud 18 is then returned to the wellbore.

More specifically, the mud from the shakers 21a and 21b is mixed together and the drilling mud sample 12a is taken out of the drilling mud line.

The drilling mud sample 12b is taken after treatment by the shakers 21a and 21b, and centrifuges 37a and 37b.

In embodiments a drilling mud pit 5 can be positioned between the shakers and the centrifuge and the drilling mud sample 12b can pass through the drilling mud pit 5 as well.

The drilling mud sample 12c is taken after the shakers 21a and 21b, the centrifuges 37a and 37b and a suction pit 35. The shakers, centrifuges and suction pit are part of the processes for cleaning the drilling mud as moved by the mud pumps.

The particle size analyzer 22 can receive and analyze the drilling mud samples 12a-12c. The particle size analyzer produces data 20 which includes producing particle size distribution curves for each of the plurality of drilling mud samples 12a-12c.

In embodiments, the particle size analyzer measures sequentially a plurality of drilling mud samples 12a-12c from the used drilling mud 14 from the wellbore 16.

The particle size distribution curve depicts the size of particles in the drilling mud sample against a passing rate percent.

The term "passing rate percent" as used herein refers to a percent of particles smaller than a preset diameter contained in the drilling mud sample.

The particle size distribution curve depicts a percent volume in the drilling mud sample. The term "percent volume" as used herein refers to a percent of volume of particles that match a specific size diameter.

The data, which can include information for generating particle size distribution curves, can be sent to an administrative processor 25 with an administrative data storage 27.

Figure 7:
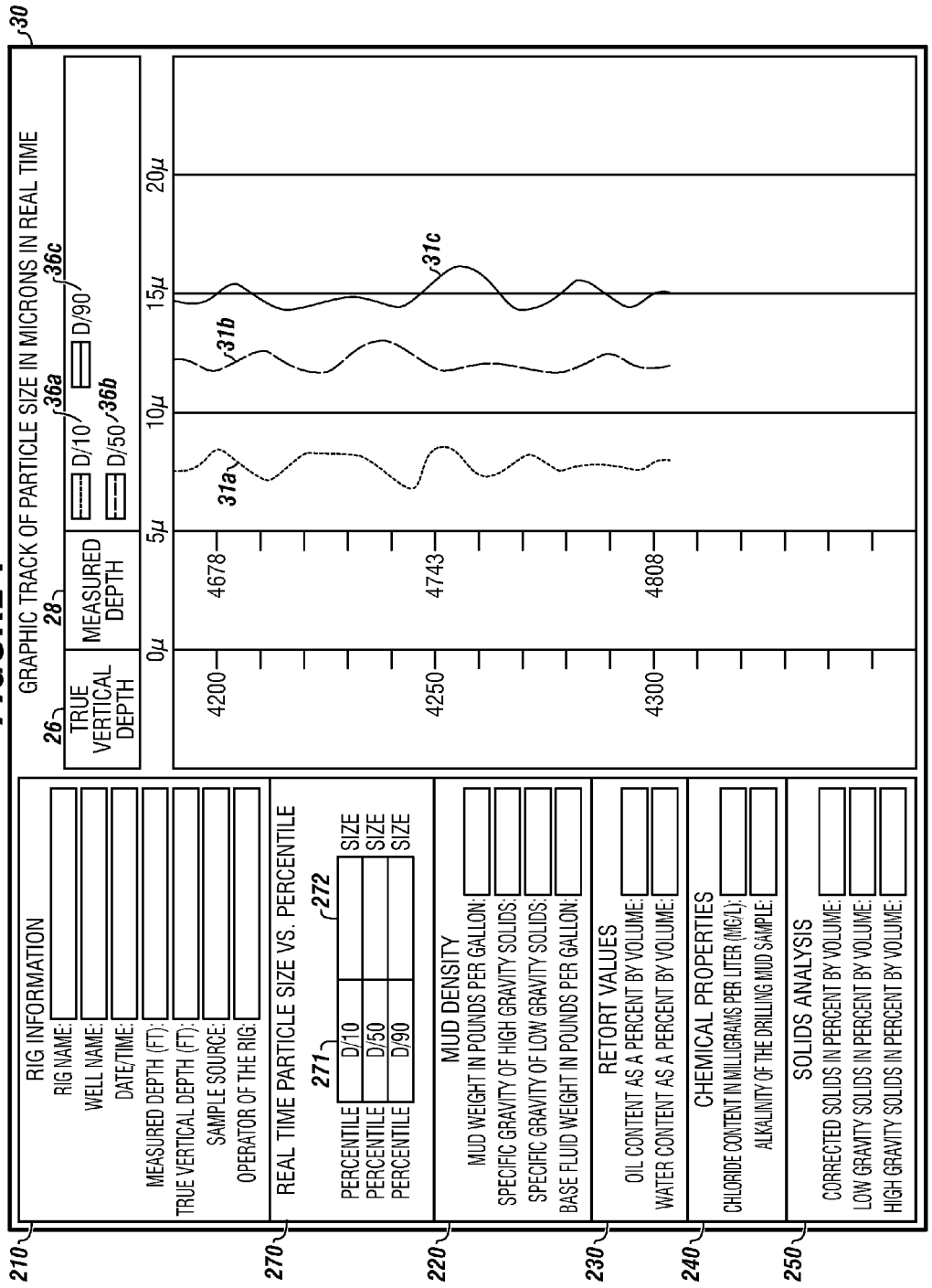
FIG. 7 depicts a graphical particle size log with wellbore information and graphical tracks of particle sizes.

Computer instructions in the administrative data storage 27 can create a particle size log which is shown in FIG. 7.

The particle size log depicts the particle size distribution curve for the plurality of drilling mud samples compared to at least one of: the true vertical depth and the measured depth of the wellbore.

The true vertical depths and measured depths are obtained from a measurement while a drilling processor 10 that receives and computes measurement while drilling data from the wellbore as a drill bit drills the wellbore.

The particle size log presents at least one graphic track for displaying the particle size distribution against depth simultaneously.

The measurement while drilling processor 10 can be connected to the administrative processor 25. The measurement while drilling processor 10 can receive and compute measurements while drilling data from the wellbore as the drill bit drills the well.

The administrative processor 25, the measurement while drilling processor 10, and a client device 3 can be connected to a network 7. Also shown are lines of communication 29a, 29b, 29c, and 29d between the administrative processor and various pieces of solids handling equipment. This communication can be wired or wireless in embodiments.

FIG. 2 depicts a user interface for inputting well fluid information to the administrative data storage.

The well fluid information user interface allows multiple entries of well fluid information 200 to the administrative data storage. The well fluid information 200 can include: rig information 210 and drilling fluid properties 218.

The rig information 210 can include rig name 211; well name 212; date/time 213; measured depth 28; true vertical depth 26; sample source 216, which refers to the respective drilling mud sample; and operator of the rig 217.

The drilling fluid properties 218 can include mud density 220, retort values 230, chemical properties 240 of the drilling mud, and solids analysis 250 of the drilling mud.

The mud density 220 can include information on mud weight in pounds per gallon 221, specific gravity of high gravity solids 222, specific gravity of low gravity solids 223, and base fluid weight in pounds per gallon 224.

The retort values 230 can include oil content as a percent by volume 231 and water content as a percent by volume 232.

The chemical properties 240 can include chloride content in milligrams per liter (Mg/L) 241 and alkalinity of the drilling mud sample 242.

The solids analysis 250 can include corrected solids in percent by volume 251; low gravity solids in percent by volume 252, and high gravity solids in percent by volume 253.

The well fluid entry, although shown as a single entry, can actually provide a multi-entry user input screen that enables all the information from all the well fluid information connected to the wellbore to be input and viewed simultaneously in a single display. A user can see the well fluid data by both depth and sample point simultaneously.

The multi-entry user input ensures the data on the drilling mud is consistent, making this invention more reliable than data input and review which is sequential.

FIG. 3 depicts a user interface for inputting solids control equipment information to the administrative data storage.

The solids control equipment information user interface allows multiple entries of solids control equipment information 300 to the administrative data storage. The solids control equipment information can include a shaker 1 interface 310, shaker 2 interface 320, centrifuge 1 interface 330, and a centrifuge 2 interface 340.

The shaker 1 interface 310 can include a manufacture name 311, model number 312, first shaker screen 313, second shaker screen 314, third shaker screen 315, and fourth shaker screen 316. The shaker 1 interface 310 can also include a time stamp 317 which indicates a time that a shaker screen was last replaced and a date stamp 318 which indicates a date when a shaker screen was last replaced.

The shaker 2 interface 320 can include a manufacture name 321, model number 322, first shaker screen 323, second shaker screen 324, third shaker screen 325, and fourth shaker screen 326. The shaker 2 interface 320 can also include a time stamp 327 which indicates a time that a shaker screen was last replaced and a date stamp 328 which indicates a date when a shaker screen was last replaced.

The centrifuge 1 interface 330 can include a manufacture name 331, model number 332, and an indication of gravity provided by the centrifuge which can be either a high gravity force or a low gravity force 333.

The centrifuge 2 interface 340 can include a manufacture name 341, a model number 342, and an indication of gravity provided by the centrifuge which can be either a high gravity force or a low gravity force 343.

The multi-entry user input screen enables all the information from all the solids control equipment connected to the wellbore to be input and viewed simultaneously in a single display. The multi-entry user input ensures the data on the drilling mud is consistent making this invention more reliable than data input and review which is sequential.

Figure 4:
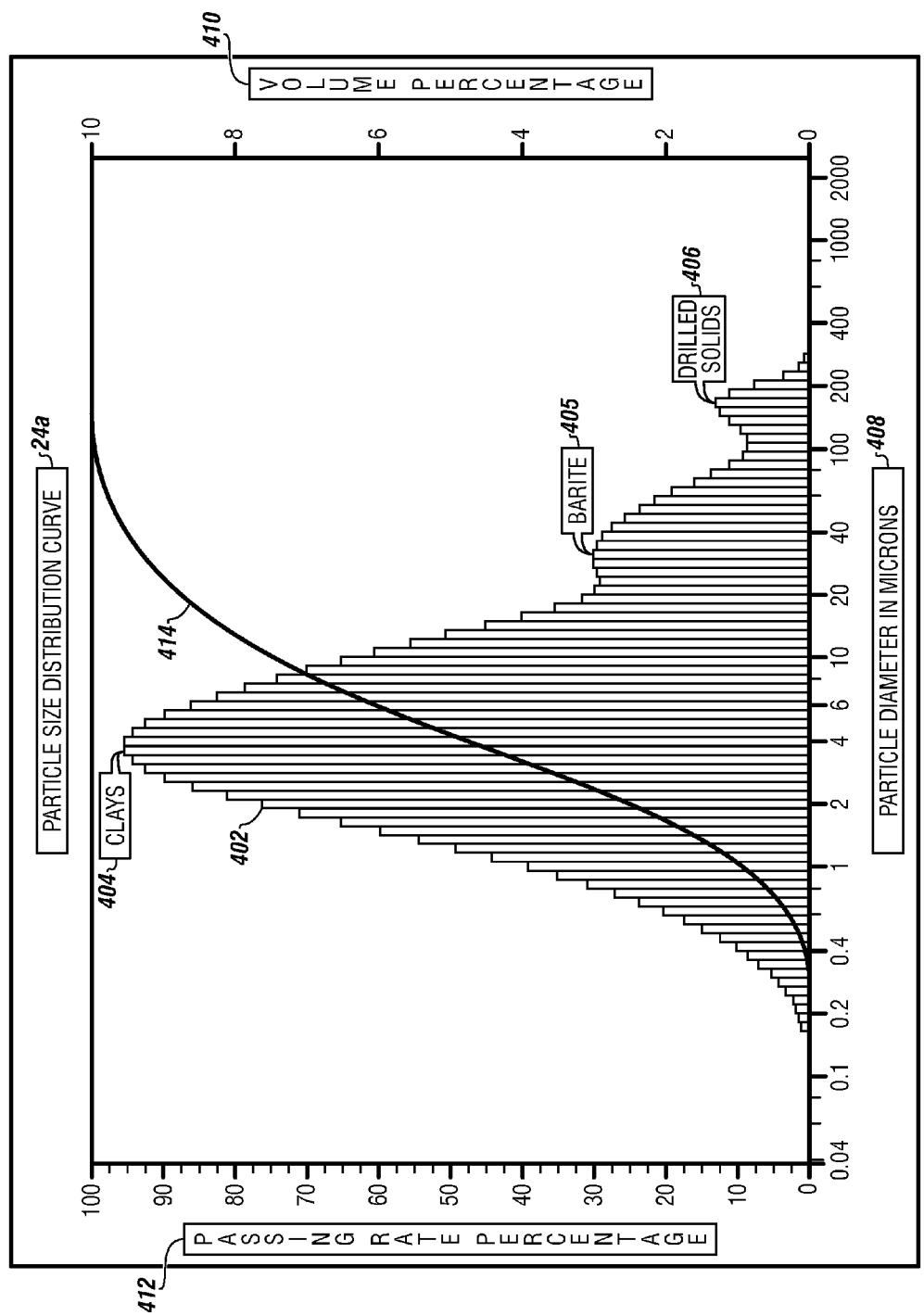
FIG. 4 depicts a particle size distribution curve for a drilling mud sample which has not been treated by a shaker or a centrifuge.

FIG. 4 depicts a particle size distribution curve for a drilling mud sample which has not been treated by a shaker or a centrifuge.

The particle size distribution curve 24a can be a trimodel curve that is presented consisting of clays 404, barite 405, and drilled solids 406.

The particle size distribution curve 24a is presented with the x-axis as particle diameter in microns 408, a right y-axis as a percent volume 410, and a left y-axis as a passing rate percent 412.

The particle size distribution curve 24a can display a volume distribution curve 402, which represents the percent volume of a particular particles size matches as specific size diameter, such as 7 percent volume of the drilling mud samples matches a 10 micron particles size.

The particle size distribution curve 24a can also display a percent passing curve 414, which represents the passing percent of a particular size particle, such as 70 percent of particles are smaller than 10 microns for a given sample.

Figure 5:
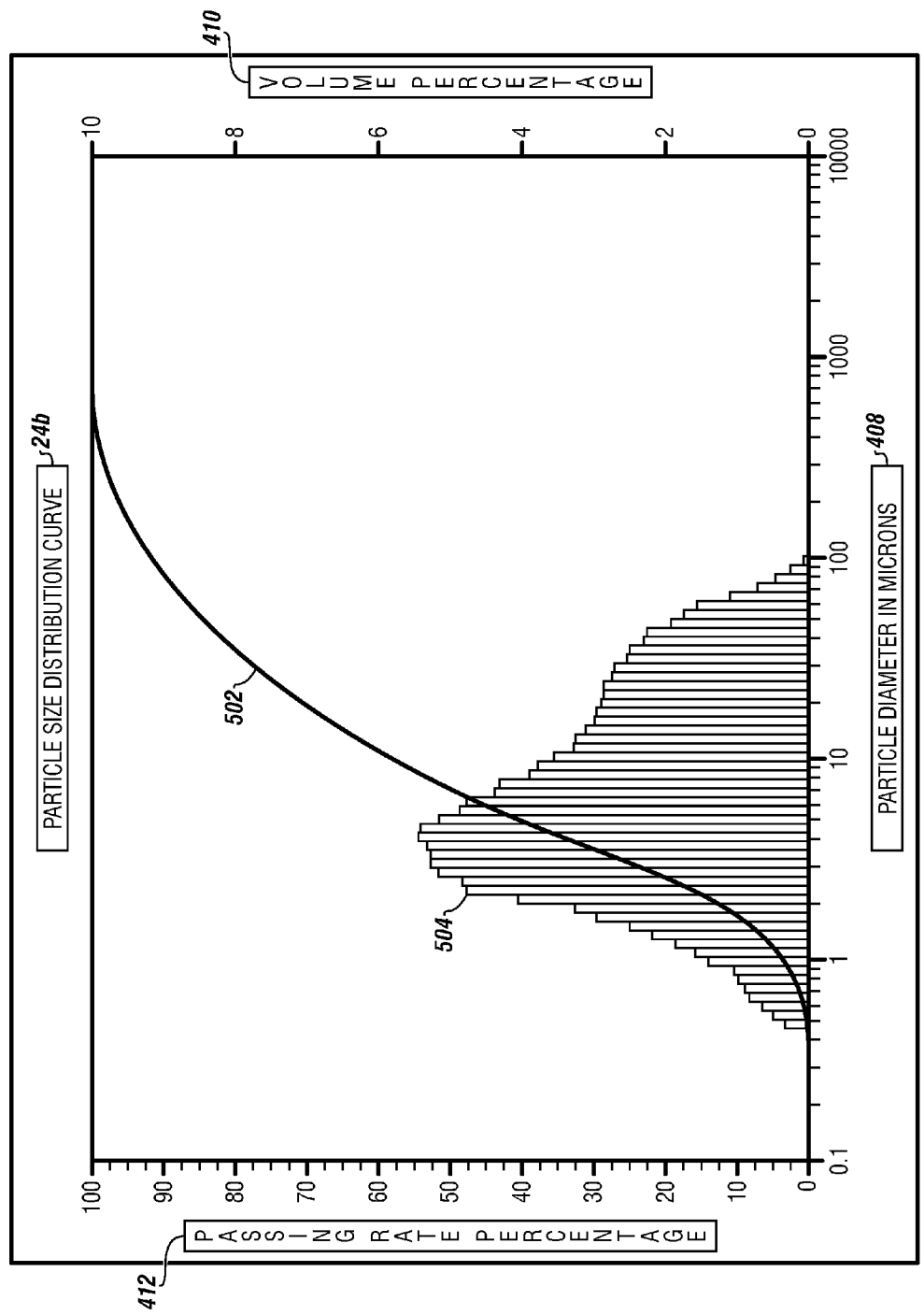
FIG. 5 depicts a particle size distribution curve for a drilling mud sample which has been treated by a shaker.

FIG. 5 depicts a particle size distribution curve of a drilling mud sample which has been treated by a shaker.

The particle size distribution curve 24b is presented with the x-axis as particle diameter in microns 408, a right y-axis as a percent volume 410, and a left y-axis as a passing rate percent 412.

The particle size distribution curve 24b is shown after some coarser particles have been separated from the drilling fluid by shale shakers which is part of the solids control equipment process.

In this embodiment, all of the particles larger than 100 microns have been separated from the drilling fluid and discarded by the shale shakers as waste to be appropriately disposed of.

Two peaks remain on this particle size distribution curve 24b, which are the pulverized drilling solids and weighting agents.

A percent passing curve 502 represents the passing percent of a particular size particle.

A volume distribution curve 504 represents the percent volume of a particular particle size that matches a specific size diameter.

Figure 6:
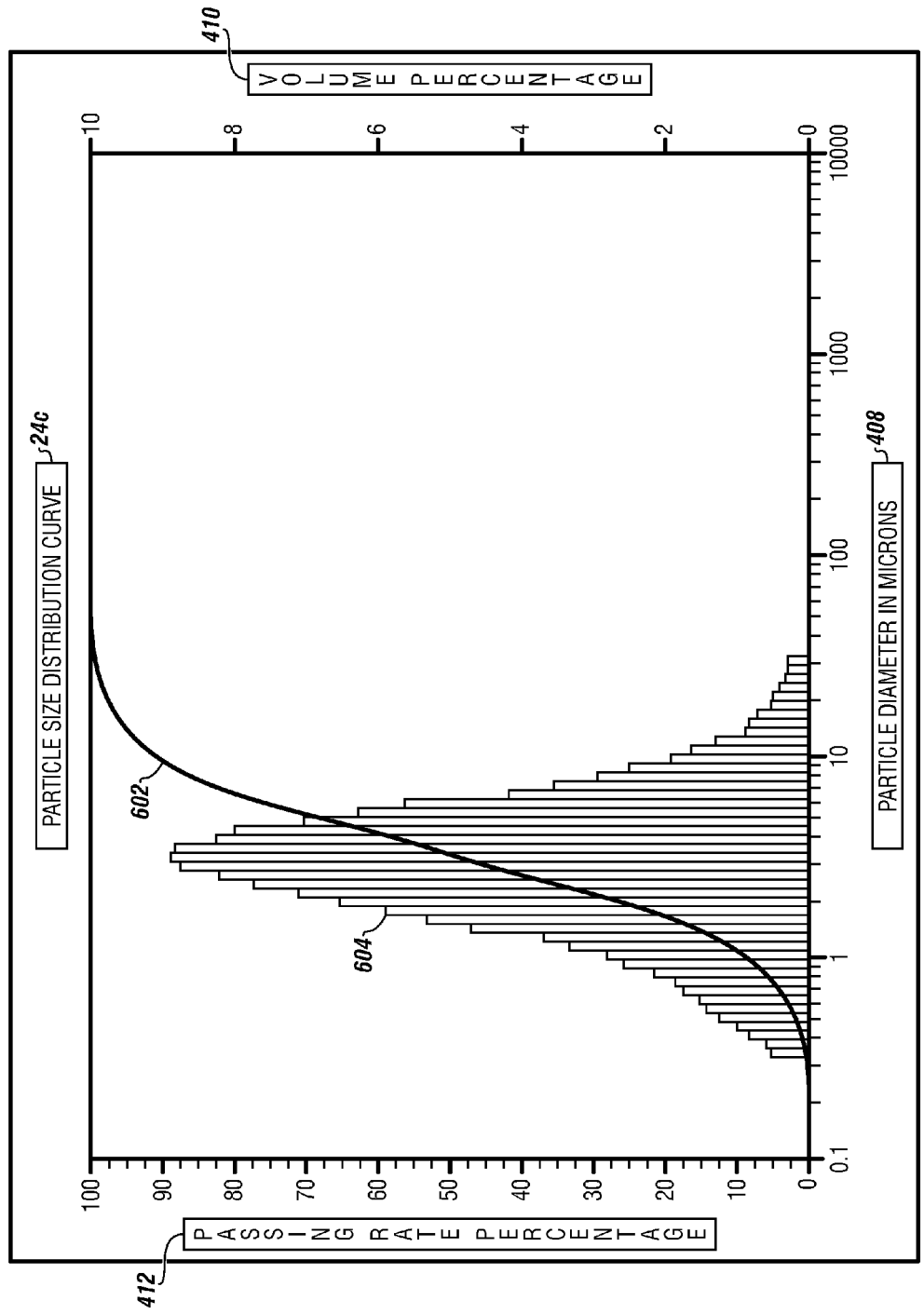
FIG. 6 depicts a particle size distribution curve for a drilling mud sample which has been treated by a shaker and a centrifuge.

FIG. 6 depicts a particle size distribution curve for a drilling mud sample which has been treated by a shaker and a centrifuge.

The particle size distribution curve 24c is presented with the x-axis as particle diameter in microns 408, a right y-axis as a percent volume 410, and a left y-axis as a passing rate percent 412.

After the drilling fluid is passed through the additional solids control equipment that includes a decanting centrifuge(s) or equivalent mechanical solids control equipment, this particle size distribution curve 24c depicts the desired state of particle size analysis for optimized drilling fluids efficiency.

A percent passing curve 602 depicts the passing percent of a particular size particle, such as 90 percent of the particles are smaller than 10 microns for a given sample.

A volume distribution curve 604 depicts the percent volume of a particular particle size that matches a specific size diameter, such as 2 percent volume of the particles found in the drilling mud sample are between 9 and 10 microns in diameter in particle size.

To reach the particle size distribution curve of FIG. 6, there may be the addition of weighting agents to the drilling fluid to maintain the proper balance in the wellbore between the drilling fluid hydrostatic head and the formation pressure.

The weighting agents are ground to a size of preferably 2 or less microns, but no greater than 6 microns.

However, it is important to note that the 6 microns is the desired cut point and may not be achievable but the goal is still to get as close, at, or below the 6 microns as the surface control equipment will allow.

FIG. 7 depicts a graphical particle size log with wellbore information and graphical tracks of particle sizes.

The particle size log 30 can be generated by computer instructions in the administrative data storage.

The particle size log 30 depicts the particle size distribution for each of the plurality of drilling mud samples, shown as graphic tracks 31a-31c that graphically depict particle size, compared to at least one of: the true vertical depth 26 and the measured depth 28 of the wellbore.

The true vertical depths and measured depths are obtained from a measurement while a drilling processor that receives and computes measurement while drilling data from the wellbore as a drill bit drills the wellbore.

Additionally, the graphical particle size log 30 can simultaneously display rig information 210, mud density 220, retort values 230, chemical properties 240 and solids analysis 250.

The graphical particle size log 30 can also display a real time particle size versus percentile graph 270, which shows percentile of particle size 271 and size in units 272, such as microns.

The graphical particle size log 30 can display a particle size distribution $-10^{th\ percentile\ distribution}$ 36a; particle size distribution $-50^{th}$ percentile distribution 36b; and particle size distribution $-90^{th}$ percentile distribution 36c.

FIG. 8 depicts a warning message on a display screen.

A display screen 800 shows the warning message 802 with a text warning that is produced by computer instructions in the administrative data storage.

The warning message presents symptoms 805 and probable causes 806a, and 806b, such as screen hole, screen tensioning which are generated by computer instructions in the administrative data storage.

The warning message 802 displays at least one corrective action 808 suggestion, such as "visual inspection to ensure no holes in screen." Another corrective action can be "perform a visual inspection to ensure shakers are properly maintained." The corrective actions are generated by computer instructions that select actions from a library of corrective actions in the administrative data storage.

Figure 9:
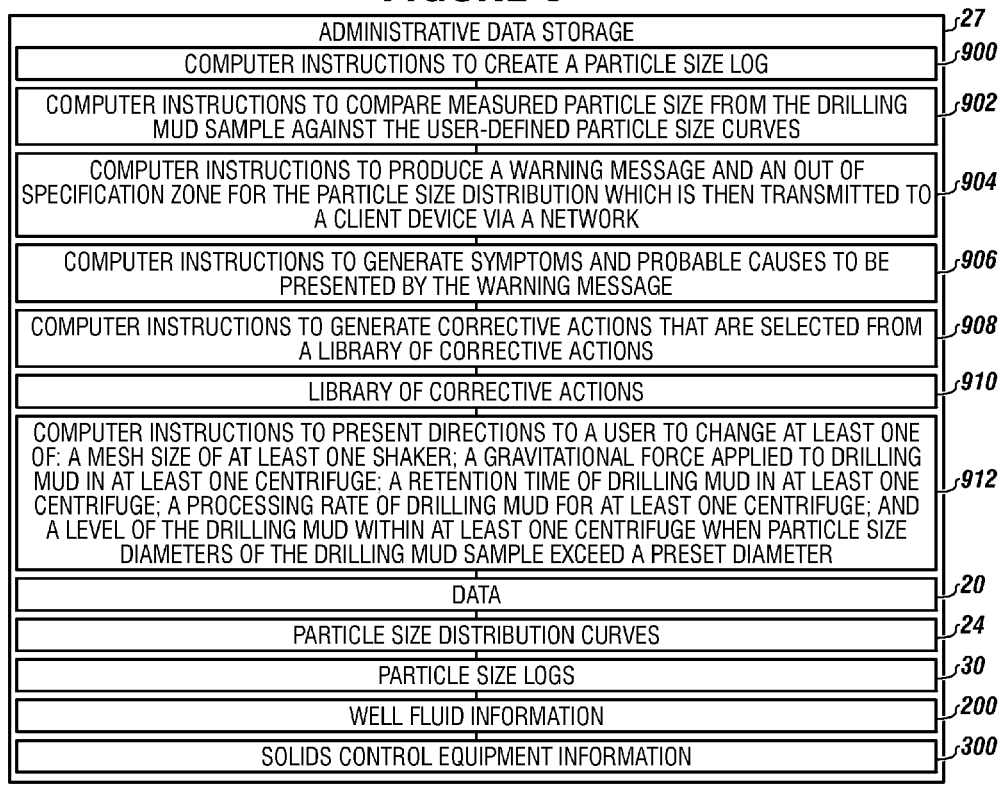
FIG. 9 depicts the administrative data storage usable with an embodiment of the method.

FIG. 9 depicts the administrative data storage usable with an embodiment of the method.

The administrative data storage 27 can include computer instructions 900 to create a particle size log.

The particle size log can graphically depict the particle size distribution for the plurality of drilling mud samples to at least one of: the true vertical depth and the measured depth of the wellbore, wherein the true vertical depth and measured depth are obtained from a measurement while drilling processor that receives and computes measurement while drilling data from the wellbore as a drill bit drills the wellbore.

The administrative data storage 27 can include computer instructions 902 to compare measured particle size from the drilling mud sample against the user-defined particle size curves.

The administrative data storage 27 can include computer instructions 904 to produce a warning message and an out of specification zone for the particle size distribution which is then transmitted to a client device via a network.

The administrative data storage 27 can include computer instructions 906 to generate symptoms and probable causes to be presented by the warning message.

The administrative data storage 27 can include computer instructions 908 to generate corrective actions that are selected from a library of corrective actions.

The administrative data storage 27 can include a library of corrective actions 910.

The administrative data storage 27 can include computer instructions 912 to present directions to a user to change at least one of: a mesh size of at least one shaker; a gravitational force applied to drilling mud in at least one centrifuge; a retention time of drilling mud in at least one centrifuge; a processing rate of drilling mud for at least one centrifuge; and a level of the drilling mud within at least one centrifuge when particle size diameters of the drilling mud sample exceed a preset diameter.

The administrative data storage 27 can also include data 20 from the particle size analyzer, particle size distribution curves 24, particle size logs 30, well fluid information 200, and solids control equipment information 300.

FIG. 10A depicts a particle size distribution curve associated with Example 1, which is associated with an excess amount of particle solids larger than 44 microns.

Example 1

The particle size distribution curve showed an excessive amount of solids larger than 44 microns to a specific screen size.

The invention analyzes the data and determines that there is an excessive amount of solids larger than the minimum cut point of the shaker screen.

The invention determines two potential approximate causes of the problem: (1) There could be a hole in the screen and/or (2) the screen was improperly installed.

The invention determines that these problems can be caused by (1) incorrect deck angle for the shaker causing inappropriate screen flooding and/or (2) insufficient g-force being transferred to the deck due to poor equipment maintenance.

Based on this analysis, the invention recommends these corrective actions to correct these causes: perform a visual inspection to determine if there are holes in the shaker screen. If there are holes in the shaker screen, replace shaker screen. Perform a visual inspection to ensure that 80 percent of the deck is flooded. If 80 percent of the deck is not flooded, adjust deck angle accordingly. Perform a visual inspection to ensure that the shaker is being properly maintained for maximum g-force transfer to shaker deck.

Figure 10B:
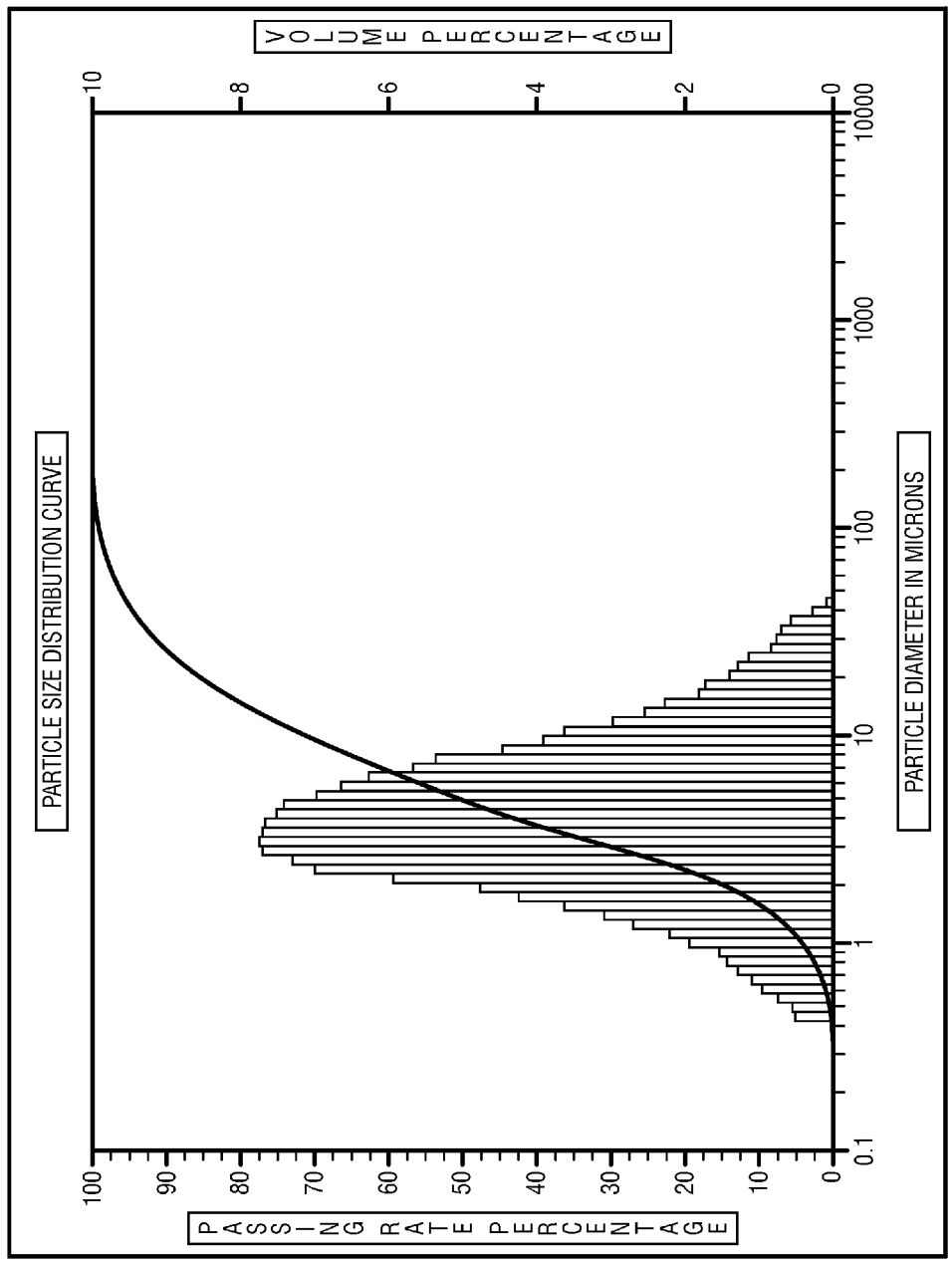
FIG. 10B depicts a particle size distribution curve for Example 1 after the corrective actions are executed.

FIG. 10B depicts a particle size distribution curve for Example 1 after the corrective actions are executed.

Figure 11:
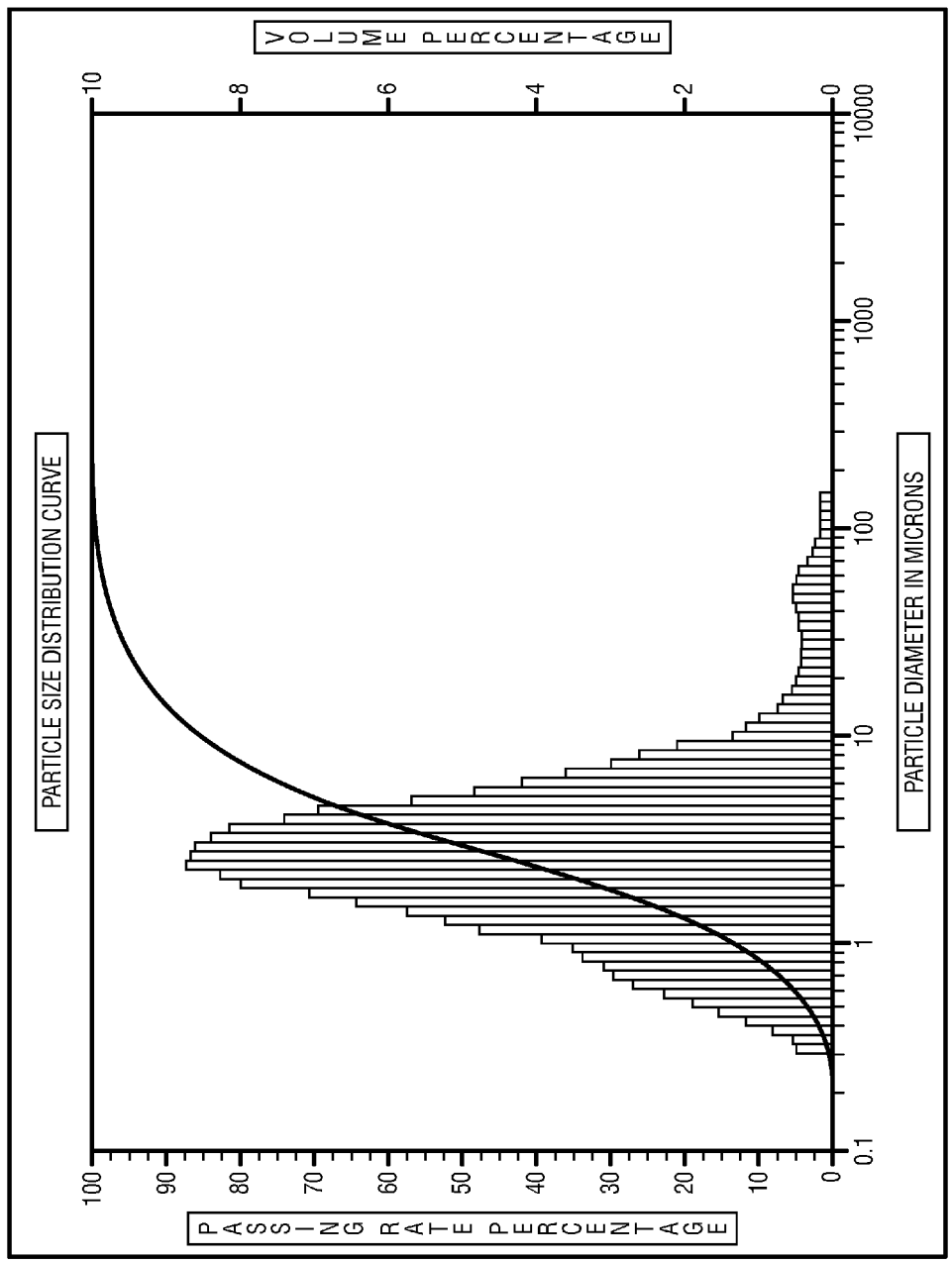
FIG. 11 depicts a particle size distribution curve associated with Example 2.

FIG. 11 depicts a particle size distribution curve associated with Example 2, which is associated with an excess amount of particle solids larger than 10 microns.

Example 2

The particle size distribution curve showed an excessive amount of solids above 10 microns in mud cleaned by centrifuge.

The invention analyzes the data and determines that there is an excessive amount of solids larger than the minimum cut point of the centrifuge. The invention determines three potential approximate causes of the problem: (1) gravity force retention time is too low; (2) solids retention time is too low: (3) viscosity too high; and (4) total concentration of the solids in the mud is too high.

The invention determines that these problems can be caused by (1) too low rotations per minute; (2) too low of a level of drilling mud within at least one centrifuge; (3) too high of a feed rate; and (4) too high of mud density.

Based on this analysis, the invention recommends these corrective actions to correct these causes: increase rotations per minute on the centrifuge; increase g-force on the centrifuge; increase retention time of solids within the centrifuge; and dilute centrifuge feed with base fluid.

These steps will be repeated until the method of the invention determines that particle size distribution no longer an excessive amount of solids above 10 microns. FIG. 6 shows the particle size distribution after the corrective actions are executed.

Figure 12:
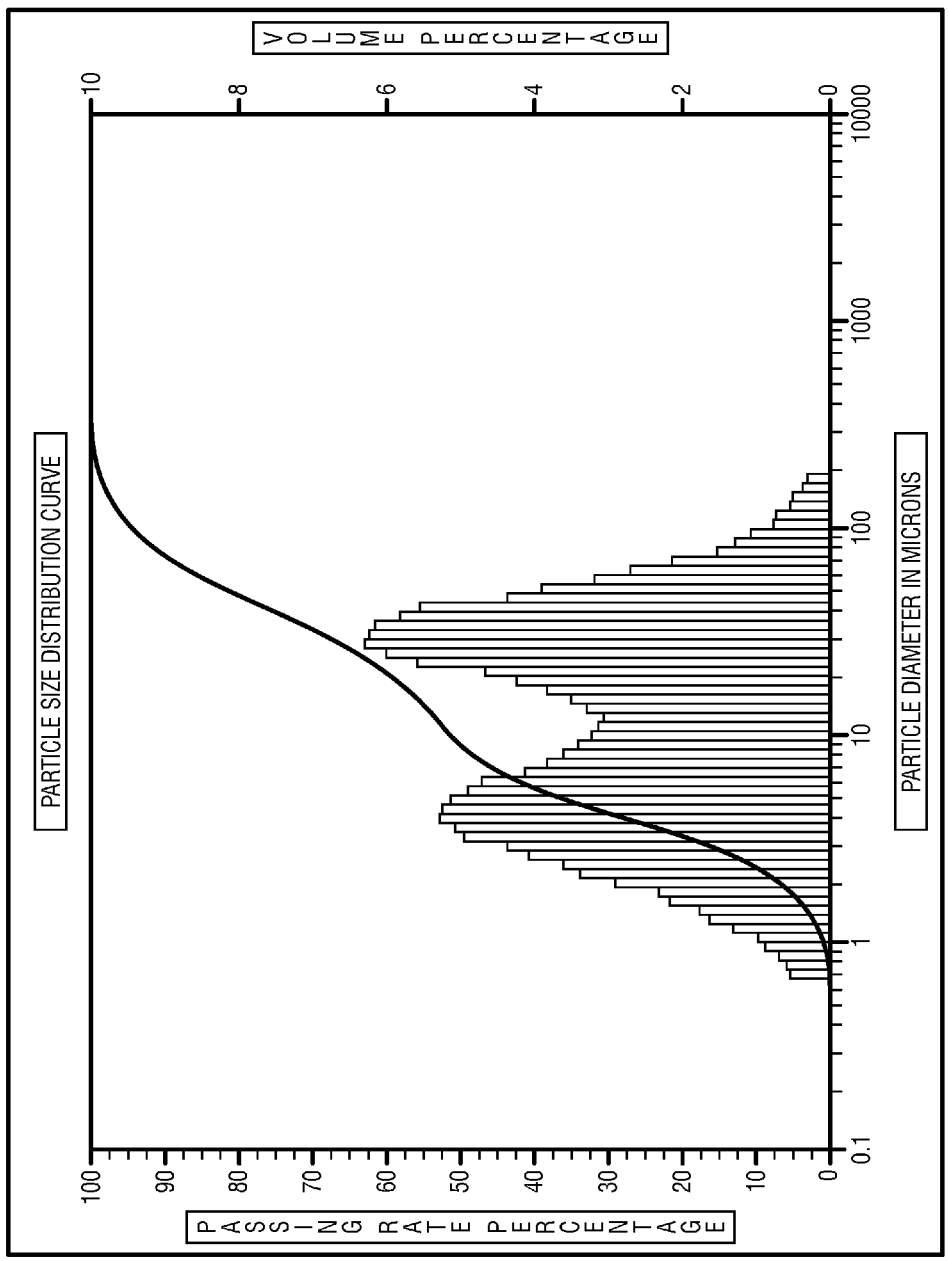
FIG. 12 depicts a particle size distribution curve associated with Example 3.

FIG. 12 depicts a particle size distribution curve associated with Example 3, which is associated with an excess amount of particle solids larger than 10 microns after centrifuge cleaning.

Example 3

The particle size distribution curve showed an excessive amount of solids above 10 microns in mud cleaned by centrifuge in a weighted system.

The invention analyzes the data and determines that there is an excessive amount of solids larger than the minimum cut point of the centrifuge.

The invention determines three potential approximate causes of the problem: (1) gravity force retention time is too low; (2) solids retention time is too low: (3) viscosity too high; and (4) total concentration of the solids in the mud is too high.

The invention determines that these problems can be caused by (1) too low rotations per minute; (2) too low of a drilling mud within at least one centrifuge; (3) too high of a feed rate; and (4) too high of mud density.

Based on this analysis, the invention recommends these corrective actions to correct these causes: increase rotations per minute on the centrifuge; increase g-force on the centrifuge; increase retention time of solids within the centrifuge; dilute centrifuge feed with base fluid.

These steps will be repeated until the Invention determines that particle size distribution no longer has an excessive amount of solids above 10 microns. FIG. 6 shows the particle size distribution after the corrective actions are executed.

Figure 13:
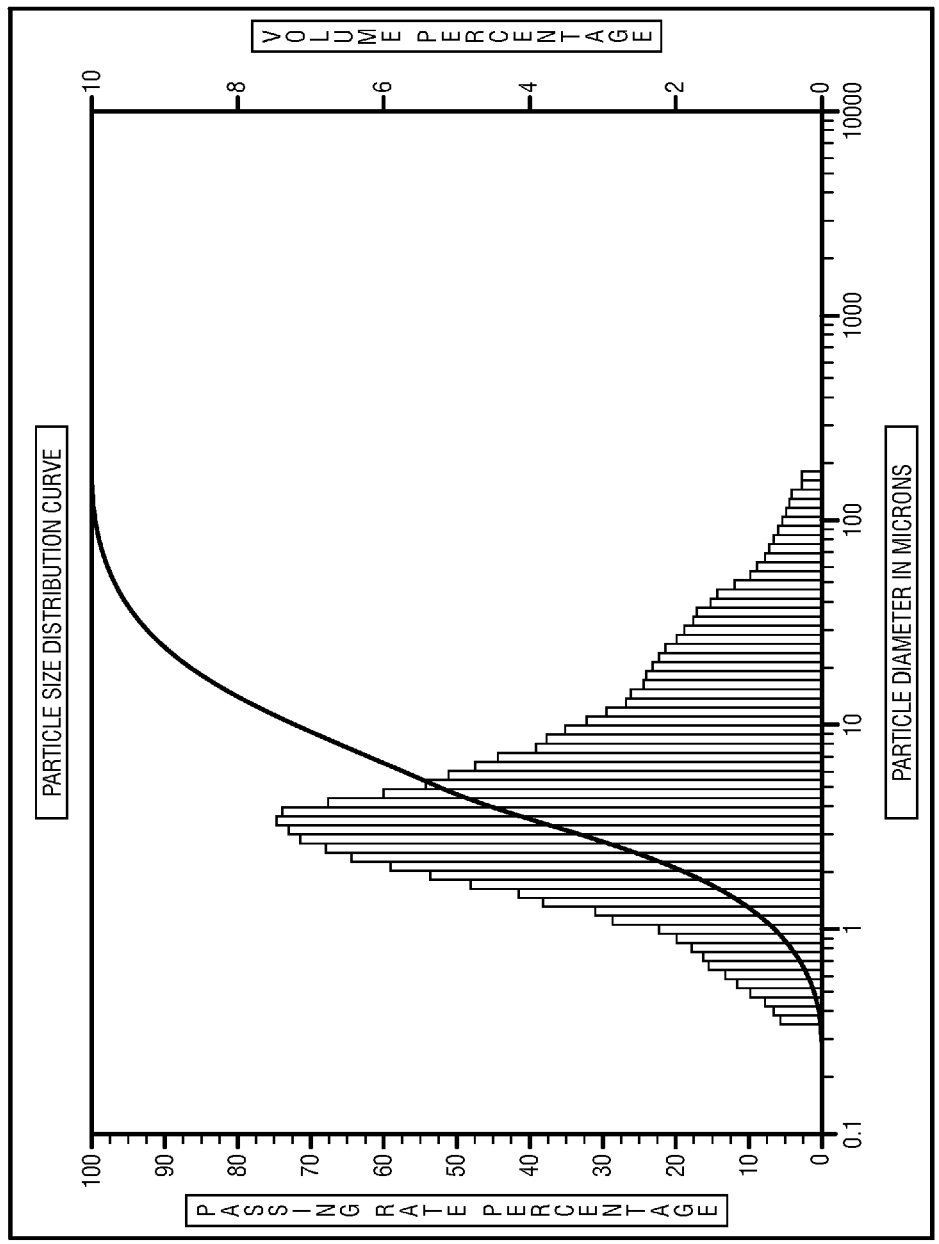
FIG. 13 depicts a particle size distribution curve associated with Example 4.

FIG. 13 depicts a particle size distribution curve associated with Example 4, which is associated with an excess amount of particle solids larger than 10 microns after centrifuge cleaning.

Example 4

The particle size distribution curve showed an excessive amount of solids above 10 microns in mud cleaned by centrifuge in a weighted system.

The invention analyzes the data and determines that there is an excessive amount of solids larger than the minimum cut point of the centrifuge for particle separation. The Invention determines three potential approximate causes of the problem: (1) gravity force retention time is too low; (2) solids retention time is too low: (3) viscosity too high; and (4) total concentration of the solids in the mud is too high.

The invention determines that these problems can be caused by (1) too low rotations per minute; (2) too low of a drilling mud within at least one centrifuge; (3) too high of a feed rate; and (4) too high of mud density.

Based on this analysis, the invention recommends these corrective actions to correct these causes: increase rotations per minute on the centrifuge; increase g-force on the centrifuge; increase retention time of solids within the centrifuge; dilute centrifuge feed with base fluid.

These steps will be repeated until the invention determines that particle size distribution no longer has an excessive amount of solids above 10 microns.

FIG. 6 shows the particle size distribution after the corrective actions are executed.

Ultimately, enhancements to this invention will utilize artificial intelligence to provide a closed loop, automated system for analyzing and obtaining the unique particle size distribution curve through the solids control equipment used in normal operation on a drilling rig along with automatically modifying the mud properties i.e. density, viscosity, plastic viscosity, yield point, salinity, alkalinity, electric stability, hardness, gel strength, oil/water ratio, corrected solids, total solids, and cake thickness.

In embodiments the invention can have an automated knowledge-based system for rig personnel or other users to improve the operation in a timelier manner to maintain the proper particle size distribution.

In embodiments, the equipment can be installed on a drilling rig and will allow for the continuous monitoring of the particle size distribution curve within the drilling fluid being transported down the drill bit to arrive at the drill bit to increase the efficiency between the drill bit and the formation, lubricate the drill bit and remove cuttings back to the surface.

While these embodiments have been described with emphasis on the embodiments, it should be understood that within the scope of the appended claims, the embodiments might be practiced other than as specifically described herein.

What is claimed is:

1. A computer implemented method for determining drilling mud particle size for a plurality of drilling mud samples from a used drilling mud from a wellbore prior to returning cleaned drilling mud downhole into the wellbore, the method comprising an administrative processor in electronic communication with an administrative data storage, wherein the administrative data storage comprises computer instructions instructing the administrative processor to:
   a. acquire data from a particle size analyzer, wherein the particle size analyzer measures sequentially a plurality of drilling mud samples taken from the used drilling mud from the wellbore;
   b. plot at least one particle size distribution curve for each of the plurality of drilling mud samples, wherein the particle size distribution curve comprises at least one of: a percent passing curve and a volume distribution curve by plotting a particle diameter in microns in each of the plurality of drilling mud samples against a passing rate percentage for particle sizes in the drilling mud sample, and against a volume percentage respectively;
   c. create a graphical particle size log comprising data from the particle size distribution curve and, at least one of: a true vertical depth and a measured depth of the wellbore, wherein the true vertical depth and the measured depth are obtained from a measurement while drilling processor in electronic communication with the administrative processor, wherein the measurement while drilling processor receives and computes measurement while drilling data from the wellbore as a drill bit drills the wellbore;
   d. display the particle size distribution of particle sizes against true vertical depths and measured depths simultaneously on the graphical particle size log;
   e. present rig information and drilling fluid properties on the graphical particle size log with the particle size distribution against depth enabling simultaneous viewing of well fluid data by depth and drilling mud sample;
   f. present a user interface for solids control equipment enabling information from solids control equipment connected to the wellbore to be inputted and viewed simultaneously with the graphical particle size log, wherein the user interface further displays in real time at least one of: particle size versus percentile and particle size versus size in units;

g. allow a user to determine a user-defined size of undesirable particulates using the presented user interface; and h. allow a user to adjust at least one particulate removal device to remove the user-defined size of undesirable particulates and create cleaned drilling mud for use in the wellbore.

2. The method of claim 1, wherein the drilling mud particle size comprises diameters of solids in the drilling mud; wherein the solids include at least one of:
a. weighting agents;
b. drilled solids from a formation through which the well is drilled;
c. viscosifiers;
d. fluid loss agents;
e. wellbore stabilizers; and
f. salt particulates.

3. The method of claim 1, wherein the data from the particle size analyzer comprises a percent volume of drilling mud particles in the drilling mud sample within a size range of the diameters of the particles in the drilling mud sample.

4. The method of claim 1 wherein the administrative data storage further comprises computer instructions instructing the administrative processor to plot a particle size distribution for the drilling mud sample identifying particle diameters and compute a percentile showing a quantity of particles that are within a specified range of diameters.

5. The method of claim 1, wherein the graphical particle size log further comprises:
a. a particle size distribution $-10^{th}$ percentile distribution;
b. a particle size distribution $-50^{th}$ percentile distribution; and
c. a particle size distribution $-90^{th}$ percentile distribution.

6. The method of claim 5, wherein the rig information comprises:
a. a rig name;
b. an operator of the rig;
c. a well name;
d. a date/time; and
e. a sample source.

7. The method of claim 6, wherein the drilling fluid properties include at least one of:
a. mud density;
b. retort values;
c. chemical properties; and
d. solids analysis.

8. The method of claim 1, wherein the administrative data storage further comprises computer instructions instructing the administrative processor to form in the graphical particle size log a real time particle size versus percentile.

9. The method of claim 1, further comprising at least one shaker, wherein multiple shakers, if used, comprise at least one different mesh size for removing different diameter particulate.

10. The method of claim 1, further comprising continuously flowing from the wellbore and analyzing used drilling mud continuously in real time, 24 hours a day, 7 days a week.

11. The method of claim 1, further comprising:
a. comparing particle size distribution curves to user-defined particle size curves and storing in the administrative data storage; and b. wherein the administrative data storage further comprises computer instructions instructing the administrative processor to present corrective options to a user to change at least one of:
(i) a mesh size of at least one shaker;
(ii) a gravity force applied to drilling mud in at least one centrifuge;
(iii) a retention time of drilling mud in at least one centrifuge;
(iv) a processing rate of drilling mud for at least one centrifuge; and
(v) a level of the drilling mud within at least one centrifuge;
when particle size diameters of the drilling mud sample exceed a preset diameter.

12. The method of claim 11, further comprising using solids control equipment information in the administrative data storage for use in presenting a text warning when a particle size diameter exceeds a preset limit, the solids control equipment information comprising:
a. a shaker 1 interface;
b. a shaker 2 interface;
c. a centrifuge 1 interface; and
d. a centrifuge 2 interface.

13. The method of claim 1, wherein an additional graphical particle size log is created based on a drilling mud sample, true vertical depth, and a measured depth from an additional wellbore.

14. The method of claim 13, wherein the administrative data storage further comprises computer instructions instructing the administrative processor to compare the graphical particle size log with the additional graphical particle size log by comparing size distributions of particles and the true vertical depth and the measured depth for each drilling mud sample in each particle size log to determine whether current drilling operations are being conducted within desired limits.

15. The method of claim 1, wherein the administrative data storage further comprises computer instructions instructing the administrative processor to: produce a text warning which indicates an out of specification zone for the particle size distribution, wherein the text warning is transmitted to at least one client device via the network.

16. The method of claim 1, wherein the administrative data storage further comprises computer instructions instructing the administrative processor to allow the user to input as one of the drilling fluid properties:
a. mud density comprising mud weight in pounds per gallon, specific gravity of high gravity solids, specific gravity of low gravity solids, and base fluid weight in pounds per gallon;
b. retort values comprising oil content as a percent by volume and water content as a percent by volume;
c. chemical properties comprising chloride content in milligrams per liter and alkalinity of the drilling mud sample; and
d. calculating solids analysis using the mud density, retort values and chemical properties and American Petroleum Institute standard equations as promulgated in 2014, forming corrected solids in percent by volume, low gravity solids in percent by volume, and high gravity solids in percent by volume for each drilling mud sample.

* * * * *